United States Patent
Yamagishi et al.

(10) Patent No.: US 6,753,527 B1
(45) Date of Patent: Jun. 22, 2004

(54) METHOD AND DEVICE FOR IMAGING LIQUID-FILLING CONTAINER

(75) Inventors: Takahiro Yamagishi, Osaka (JP); Shigeki Tamura, Osaka (JP)

(73) Assignee: Suntory Limited (JP)

( * ) Notice: Subject to any disclaimer, the term of this patent is extended or adjusted under 35 U.S.C. 154(b) by 5 days.

(21) Appl. No.: 09/937,989

(22) PCT Filed: Jan. 2, 2001

(86) PCT No.: PCT/JP01/00728

§ 371 (c)(1),
(2), (4) Date: Jan. 7, 2002

(87) PCT Pub. No.: WO01/57503

PCT Pub. Date: Aug. 9, 2001

(30) Foreign Application Priority Data

Feb. 3, 2000 (JP) .......................................... 2000-26708

(51) Int. Cl.[7] ................................................ G01J 5/02
(52) U.S. Cl. ............................. 250/339.06; 250/223 B; 250/341.8; 250/339.02; 250/339.11
(58) Field of Search ....................... 250/339.06, 339.12, 250/338.1, 339.02, 339.11, 341.7, 341.8, 577, 223 B (56) References Cited

U.S. PATENT DOCUMENTS

| | | | | |
|---|---|---|---|---|
| 3,563,379 A | * | 2/1971 | Stapf et al. ................... | 209/524 |
| 4,020,949 A | * | 5/1977 | Erdman .................... | 250/223 B |
| 4,121,103 A | * | 10/1978 | Calhoun ................ | 250/339.12 |
| 4,221,961 A | * | 9/1980 | Peyton .................... | 250/223 B |
| 4,293,219 A | * | 10/1981 | Ducloux ................ | 250/223 B |
| 4,368,980 A | * | 1/1983 | Aldred et al. ............ | 250/339.06 |
| 4,650,326 A | * | 3/1987 | Nagamine et al. ....... | 250/223 B |
| 4,733,095 A | * | 3/1988 | Kurahashi et al. ........... | 250/577 |
| 4,915,237 A | * | 4/1990 | Chang et al. ................ | 209/524 |
| 5,045,688 A | * | 9/1991 | Domenico et al. ....... | 250/223 B |
| 5,067,616 A | * | 11/1991 | Plester et al. ................ | 209/3.1 |
| 5,126,556 A | * | 6/1992 | Domenico et al. ....... | 250/223 B |
| 5,486,693 A | * | 1/1996 | Achter et al. ........... | 250/223 B |
| 6,333,512 B1 | * | 12/2001 | Wirthlin ..................... | 250/577 |
| 6,433,338 B1 | * | 8/2002 | Nordbryhn et al. ..... | 250/339.12 |
| 6,452,156 B2 | * | 9/2002 | Lindner .................. | 250/223 B |

FOREIGN PATENT DOCUMENTS

| | | |
|---|---|---|
| JP | 49-23649 | 3/1974 |
| JP | 5180288 | 7/1976 |
| JP | 53-17764 | 2/1978 |
| JP | 9-169392 | 6/1997 |
| JP | 10-206214 | 8/1998 |
| JP | 11-248645 | 9/1999 |

* cited by examiner

Primary Examiner—Diego Gutierrez
Assistant Examiner—Yaritza Guadalupe
(74) Attorney, Agent, or Firm—Webb Ziesenheim Logsdon Orkin & Hanson P.C.

(57) ABSTRACT

The present invention relates to a method and an apparatus for imaging a liquid-filling container in which a plurality of imaging devices each comprising a light emitting unit and a light receiving unit are provided. Light from each light emitting unit is irradiated onto a liquid-filling container and this light transmitted through the container is received by each light receiving unit. The object of the present invention is to provide such method and an apparatus for imaging a liquid-filling container. This method or apparatus allows for simultaneous and highly reliable imaging of two or more kinds of condition of the container. For accomplishing this object, according to the present invention, wavelengths of the lights emitted by the respective light emitting units and received by the respective light receiving units of the imaging devices for imaging the liquid-filling containers are different from each other.

20 Claims, 4 Drawing Sheets

METHOD AND DEVICE FOR IMAGING LIQUID-FILLING CONTAINER

BACKGROUND OF THE INVENTION

1. Filed of the Invention

The present invention relates to a method and an apparatus for imaging a liquid-filling container in which a plurality of imaging devices each comprising a light emitting unit and a light receiving unit are provided and light from each light emitting unit is irradiated onto a liquid-filling container and the light transmitted through the container is received by each light receiving unit.

2. Description of Prior Art

The imaging of a liquid-filling container noted above is employed in a manufacturing line of various beverages such as soft drinks or alcoholic beverages in order to inspect whether the amount of liquid as the beverage filled in a container made of glass or PET is within a predetermined range or not and/or whether any foreign substance is inadvertently mixed in the beverage filled in the container or present in the container or the material forming the container or a condition of the mouth of the liquid-filling container, or whether a cap is securely fitted on the mouth of the container or not.

Conventionally, in the case of inspection of e.g. beverage by way of imaging a liquid-filling container, a single light emitting unit emits and irradiates a visible light having a wavelength of 400 to 700 nm onto the container to be transmitted therethrough to be received by a light receiving unit comprising a CCD camera for imaging of the container, so that the inspection is effected based on the image whether the surface level of the liquid inside the container is within a predetermined range or not. And, another light emitting unit is employed for emitting a visible light of the same wavelength for determination as to whether any foreign substance is mixed in the beverage or in the container or the material forming the container or not. And, still another light emitting unit is employed for emitting the visible light of the same wavelength to be reflected by the mouth of the container or the cap and this reflected light is received by a corresponding light receiving unit for determination as to the condition of the container mouth or whether the cap is properly fitted to this mouth or not.

With the conventional imaging technique above, the light emitting units for the detection of the liquid surface level, the detection of the foreign substance present in the liquid or in the container or its material and the detection of the mouth or the attached condition of the cap to the mouth all emit a visible light of a same wavelength. Accordingly, e.g. irregular reflection of the light may occur due to the shape of the liquid-filling container to interfere as a noise with the visible light for liquid surface level detection and the visible light for the cap attachment condition detection. So that, a portion of the visible light for liquid level detection may enter the light receiving unit for cap attachment detection. Conversely, a portion of the visible light for foreign substance detection or cap attachment detection can be incident on the light receiving unit for the liquid level detection. Consequently, the detection of liquid surface level, the detection of foreign substance and detection of cap attachment can not be reliably effected simultaneously.

For improving the detection precision, it is conceivable to provide a time difference between the liquid level detection, foreign substance detection and cap attachment detection, so as to effect the liquid level detection first and to effect the detection of foreign substance or cap attachment thereafter. This, however, increases the time required for detection, inviting reduction in the production efficiency.

Another conceivable method is to block the noise by changing or shielding the sites of detection between the liquid level detection and the foreign substance or cap attachment detection. This, however, increases the space required for detection. In the case of a manufacturing line of beverage for instance, this method will make it difficult to form the manufacturing line compact and will require much cost in terms of maintenance and production efficiency.

The present invention has been devised to overcome the above-described problems of the prior art. A primary object of the invention is to provide a method and an apparatus for imaging a liquid-filing container which method or apparatus allows simultaneous and highly reliable imaging of two or more kinds of condition of the container.

SUMMARY OF THE INVENTION

Figure 1:
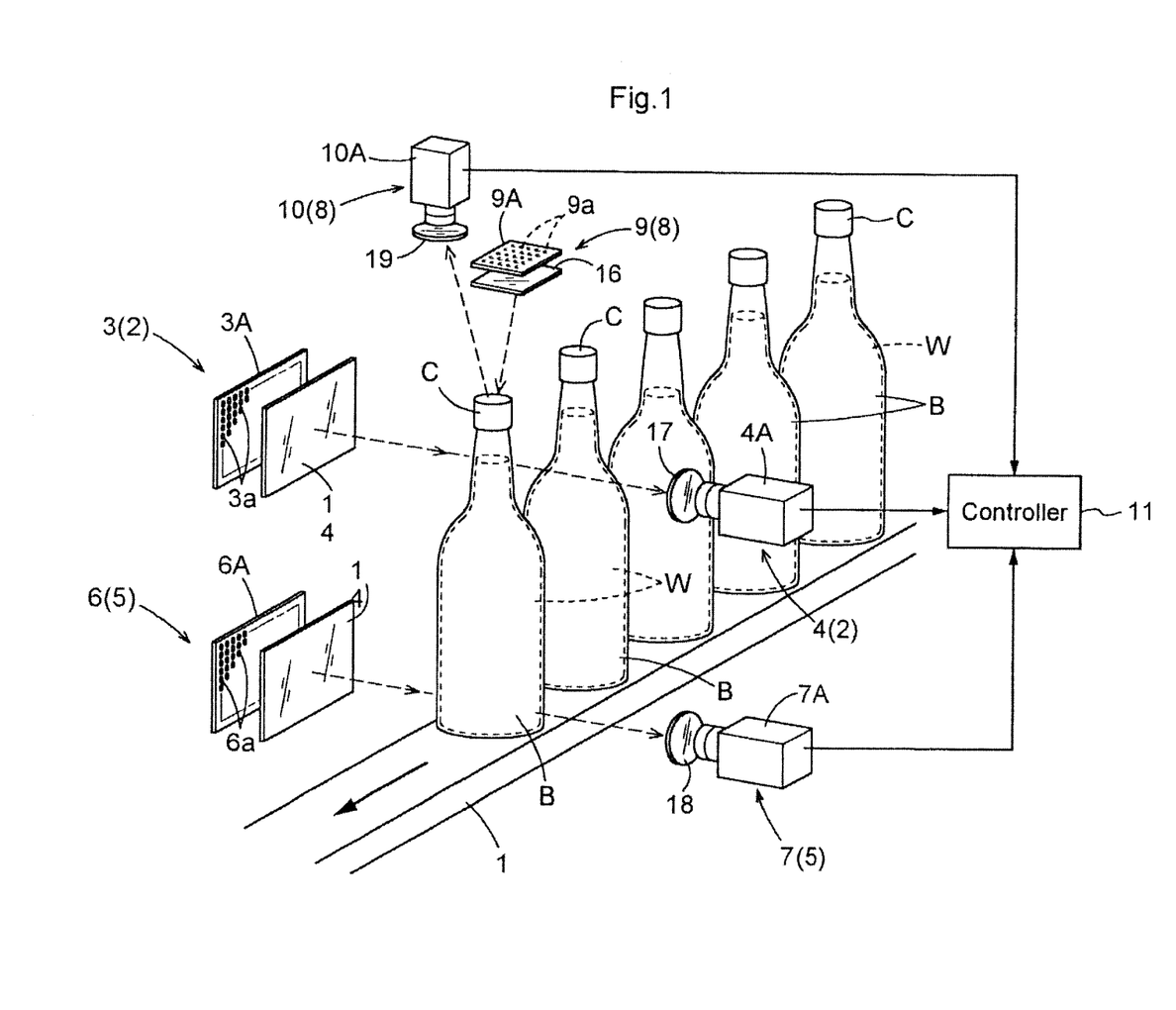
FIG. 1 is a perspective view showing an apparatus for imaging a liquid-filling container relating to the invention.
Figure 3:
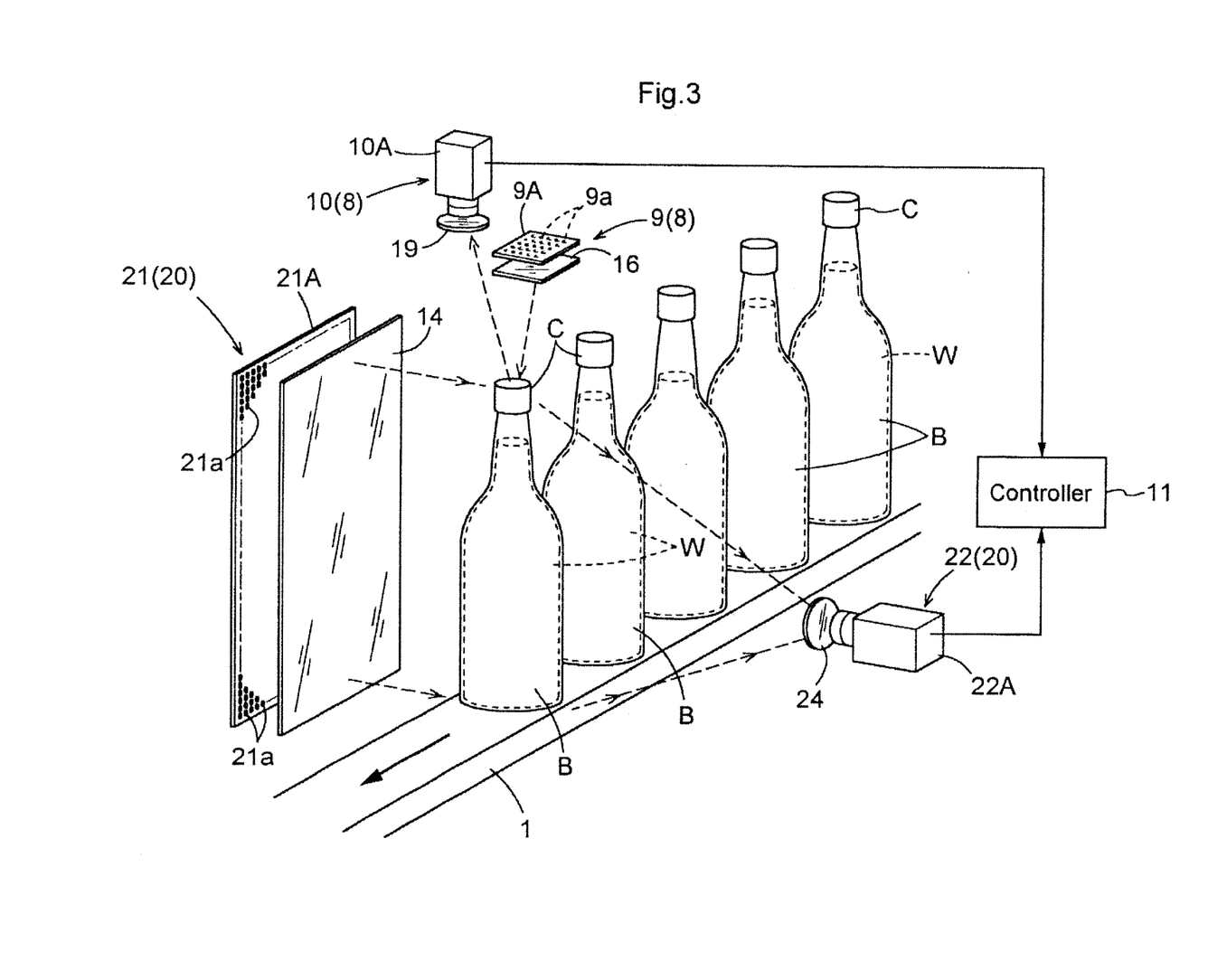
FIG. 3 is a perspective view showing an apparatus for imaging a liquid-filing container relating to a further embodiment of the invention.

According to the present invention, as shown in FIGS. 1 and 3 for example, in a method and an apparatus for imaging a liquid-filling container in which a plurality of imaging devices 2, 5, 8, 20 each comprising a light emitting unit 3, 6, 9, 21 and a light receiving unit 4, 7, 10, 22 are provided and light from each light emitting unit 3, 6, 9, 21 is irradiated onto a liquid-filling container B and this light transmitted through the container is received by each light receiving unit 4, 7, 10, 22, wherein wavelengths of the lights emitted by the respective light emitting units 3, 6, 9, 21 and received by the respective light receiving units 4, 7, 10, 22 of the imaging devices 2, 5, 8, 20 for imaging the liquid-filling containers are different from each other.

With this feature, a plurality of imaging devices each comprising a light emitting unit and a light receiving unit are provided and wavelengths of the lights emitted by the respective light emitting units and received by the respective light receiving units of the imaging devices for imaging the liquid-filling containers are different from each other. Therefore, there occurs no such trouble as light irradiated from one light emitting unit enters a light receiving unit not corresponding to this light emitting unit. Consequently, two or more kinds of conditions of the liquid-filing container may be imaged simultaneously and reliably.

According to the present invention, as shown in FIGS. 1 and 3 for example, the light emitting units 3, 6, 9, 21 respectively have light emitters 3A, 6A, 9A, 21A each capable of emitting and irradiating light of a predetermined wavelength and the light receiving units 4, 7, 10, 22 respectively have light-receiving cut filters 17, 18, 19, 24 for allowing transmission of a light in the predetermined wavelength and light receivers 4A, 7A, 10A, 22A for receiving the light transmitted through the respective light-receiving cut filters 17, 18, 19, 24 corresponding thereto.

With this feature, the light emitting units respectively have light emitters each capable of emitting and irradiating a light in the predetermined wavelength and the light receiving units respectively have light-receiving cut filters for allowing transmission of light in the predetermined wavelength and light receivers for receiving the light transmitted through the respective light-receiving cut filters corresponding thereto. Therefore, there is no need of employing a special construction as the light receiving unit. As a result, the invention may be embodied, with using a light emitter, a light receiver and a cut filter which are relatively inexpensive.

According to the present invention, as shown in FIGS. 1 and 3 for example, at least one of said light emitting units 3, 6, 9, 21 emits and irradiates near infrared light.

According to the present invention, at least one of said light receiving units 4, 7, 10, 22 receives near infrared light.

With these features, at least one of said light emitting units emits and irradiates near infrared light or at least one of said light receiving units receives near infrared light. Therefore, it is possible to detect e.g. the filled amount of the liquid, regardless of the color of the container or the color of the liquid filled inside the container.

Figure 4:
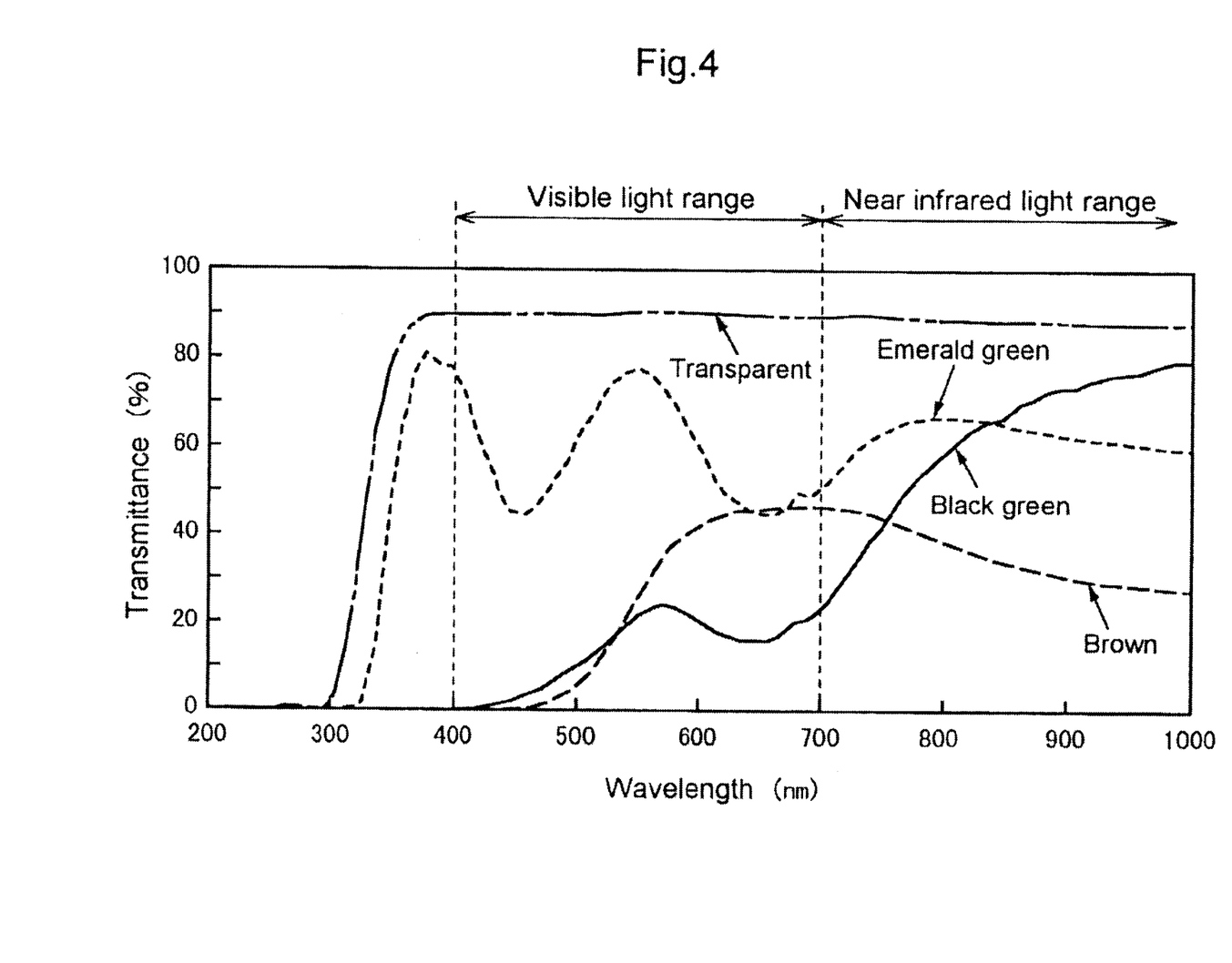
FIG. 4 is a graph showing transmittance of light.

Namely, in case the detection of the filled amount of the liquid or presence/absence of any foreign substance in the liquid or in the container or in the container forming material is effected by way of imaging the liquid-filling container by using a visible light having a wavelength of 400 nm to 700 nm as conventionally proposed, if the container has a dark color such as black, dark green or dark brown, as shown in a graph of FIG. 4 (transmittance for a glass thickness of 3 mm), the transmittance of the visible light becomes extremely low.

For this reason, when the visible light emitted from the light emitting unit is received by the light receiving unit, the portion of the visible light travelling outside the container is received substantially as it is or directly by the light receiving unit, so that the amount of received light for this area outside the container is large, whereas the amount of light corresponding to the container is extremely small. Then, since the inspection of the liquid surface of the liquid filled in the container or of the absence/presence of any foreign substance in the liquid or in the container or its material is to be effected for such area of extremely limited received light amount, the detection error becomes significant or the detection of the liquid surface or mixed foreign substance per se becomes very difficult. Further, even if the absolute light amount is increased to overcome this problem, improvement in the detection precision made possible by such measure is limited.

Further, even if the container per se does not have such dark color as black, dark green or dark brown, if the liquid filled therein has a dark color, the detection of foreign substance in the liquid becomes impossible. Moreover, if fine bubbles generated in association with the filling operation of the liquid are present near the liquid surface, the amount of light transmitted through the bubbles will be small due to the effect of diffused reflection of the light by the bubbles and also the amount of light transmitted through the liquid portion too will be limited due to the dark color, so that discrimination therebetween is difficult, thus impeding reliable detection of the liquid surface.

On the other hand, with the use of near infrared light having a wavelength of 700 to 900 nm, preferably 750 to 850 nm, even if the container has a dark color such as black, dark green or dark brown or if the filled liquid has a dark color or even if the container has a surface frosting treatment, there occurs no significant reduction in the transmittance of the near infrared light through the liquid-filling container. So that, significant reduction in the received light amount for the area corresponding to the liquid-filling container may be avoided advantageously.

Accordingly, various kinds of detection for the area corresponding to this container of the liquid surface level or of any foreign substance present in the liquid or in the container or the container material are made possible. As a result, the various conditions of the liquid-filing container can be reliably detected, regardless of the color of the container or the color of the liquid or regardless of presence/absence of bubbles near the liquid surface.

Incidentally, for imaging a liquid-filling container by irradiating light from the light emitting unit onto the container and receiving the transmitted light by the light receiving unit, or receiving the light by the light receiving unit, according to the present invention, the amount of received light at the area corresponding to the container is positively increased so as to reduce the difference in the received light amounts relative to that of the area corresponding to the outside of the container thereby to improve the detection precision. By irradiating the near infrared light alone or a greater amount of near infrared light component than visible light component of the light, a sufficient amount of near infrared light may be transmitted, depending on the color of the container or the color of the liquid filled therein. Or, by receiving the near infrared light component alone or a greater amount of near infrared component than the visible light component by the light receiving unit, a sufficient amount of near infrared light may be transmitted, depending on the color of the container or the color of the liquid filled therein.

According to the present invention, as shown in FIGS. 1 and 3 for example, each imaging device 2, 5, 8, 20 images a state of a liquid-filled container B which is conveyed one after another along a transport line 1.

With this characterizing, each imaging device images a state of a liquid-filled container which is conveyed one after another along a transport line. Therefore, for the number of liquid-filling containers being conveyed along the transport line one after another, various conditions thereof such as the filled amount, presence/absence of foreign substance in the liquid, presence/absence of foreign substance in the container or the container forming material, and the condition of the container mouth or attachment condition of a cap to the container mouth can be detected speedily and continuously.

According to the present invention, as shown in FIG. 1 for example, in the method of imaging a liquid-filling container or the apparatus for imaging a liquid-filling container, one of said plurality of imaging device 2, 5, 8 is a filled-amount detecting device 2 for detecting the filled amount of liquid W filled in the container B.

With this feature, one of said plurality of imaging devices is a filled-amount detecting device for detecting the filled amount of liquid filled in the container. Therefore, the filled amount of the liquid filled in the liquid-filling container may be detected. Especially, if near infrared light is used in this filled-amount detecting device, for the reasons described hereinbefore, even if the container has a dark color such as black, dark green or dark brown or if the filled liquid has a dark color or even if the container has a surface frosting treatment, the detection of liquid level is possible at the area corresponding to this container. As a result, the filled amount of the liquid may be detected reliably, regardless of the color of the liquid-filling container or the liquid or presence/absence of bubbles near the liquid surface.

According to the present invention, as shown in FIG. 1 for example, in the method of imaging a liquid-filling container or the apparatus for imaging a liquid-filling container, one of said plurality of imaging devices 2, 5, 8 is a liquid foreign substance detecting device 5 for detecting foreign substance present in the liquid filled in the container B.

With this feature, one of said plurality of imaging devices is a liquid foreign substance detecting device for detecting foreign substance present in the liquid filled in the container. Therefore, the presence/absence of foreign substance in the liquid filled in the liquid-filling container may be detected. Especially, if near infrared light is used in this liquid foreign substance detecting device, for the reasons described hereinbefore, even if the container has a dark color such as black, dark green or dark brown or if the filled liquid has a dark color or even if the container has a surface frosting treatment, the detection of the presence/absence of foreign substance in the liquid is possible at the area corresponding to this container. As a result, the presence/absence of foreign substance in the liquid may be detected reliably, regardless of the color of the liquid-filling container or the liquid or presence/absence of bubbles near the liquid surface.

According to the present invention, as shown in FIG. 3 for example, in the method of imaging a liquid-filling container or the apparatus for imaging a liquid-filling container, one of said plurality of imaging devices 8, 20 is a container/container-material foreign substance detecting device 20 for detecting foreign substance present in the container or in material forming the container.

With this characterizing feature, one of said plurality of imaging devices is a container/container-material foreign substance detecting device for detecting foreign substance present in the container or in material forming the container. Therefore, the presence/absence of foreign substance in the liquid-filling container or in the material forming the container may be detected. Especially, if near infrared light is used in this container foreign substance detecting device, for the reasons described hereinbefore, even if the container has a dark color such as black, dark green or dark brown or if the filled liquid has a dark color or even if the container has a surface frosting treatment, the detection of the presence/absence of foreign substance in the container or in the container material is possible at the area corresponding to this container. As a result, the presence/absence of foreign substance in the container or container material may be detected reliably, regardless of the color of the liquid-filling container or the liquid.

According to the present invention, in the method of imaging a liquid-filling container or the apparatus for imaging a liquid-filling container, one of said plurality of imaging devices 2, 5, 8, 20 is a container mouth detecting device 8 for detecting condition of a mouth of the container B or attachment condition of a cap C to the container mouth.

With this characterizing feature, one of said plurality of imaging devices is a container mouth detecting device for detecting condition of a mouth of the container or attachment condition of a cap to the container mouth. With this, needless to say, it is possible to detect condition of a mouth of the container or attachment condition of a cap to the container mouth by effectively utilizing the light reflected from the container mouth or from the cap. Moreover, even when the filled-amount detecting device, the liquid foreign substance detecting device and the container/container-material foreign substance detecting device are used at one time together, there occurs no interference therebetween, and the condition of a mouth of the container or attachment condition of a cap to the container mouth may be detected.

Incidentally, in the above description, reference marks and numerals were employed for facilitating reference to the accompanying drawings. It is understood that the provision of these marks and numerals is not to limit the invention to the constructions shown in the drawings.

DETAILED DESCRIPTION OF THE PREFERRED EMBODIMENTS

Preferred embodiments of a method and an apparatus relating to the present invention for imaging a liquid-filling container will be described next with reference to the accompanying drawings.

These method and apparatus for imaging a liquid-filling container are for use in e.g., a manufacturing or bottling line of a bottled beverage such as soft drinks or alcoholic beverages, wherein the method or the apparatus is employed for inspecting whether the container or bottle filled with beverage in the foregoing process contains a predetermined filled content of the beverage or not or whether any foreign substance or object other than the beverage may be present inside the filled bottle or not, or whether any foreign matter or substance may be present within the material forming the bottle or not, or whether any flaw is present at the mouth of the liquid-filling bottle or a cap is properly attached to this mouth or not. Such manufacturing line, as shown in FIG. 1, include a transfer conveyer 1 for conveying a plurality of liquid-filled glass containers or bottles B one after another.

The transfer conveyer 1 conveys, to a predetermined position, each liquid-filling container B which was filled, in the foregoing stage of the process, with beverage W as a liquid by an unillustrated filling device and then fitted atop with a cap by an unillustrated capping device. At an upper position across this conveyer 1 and in opposition to each other, there are disposed a light emitting unit 3 and a light receiving unit 4 together constituting a filled-amount detecting device 2 as one imaging device.

Downwardly of the filled-amount detecting device 2, there is provided a liquid foreign substance detecting device 5 as another imaging device for detecting foreign substance present in the beverage or liquid inside the liquid-filling container B. And, a light emitting unit 6 and a light receiving unit 7 together constituting this liquid foreign substance detecting device 5 for detection of foreign substance are also disposed in opposition to each other across the transfer conveyer 1.

At a further upper position of the transfer conveyer 1, there are disposed a light emitting unit 9 and a light receiving unit 10 one after another along the conveying direction of the transfer conveyer 1, the units 9, 10 together constituting a container mouth detecting device 8 as still another imaging device for detecting attachment condition of a cap C to the mouth of the liquid-fillng container B.

The light receiving unit 4 for detection of filled amount, the light receiving unit 7 for detection of liquid foreign substance and the light receiving unit 10 for detection of container mouth are all connected to a controller 11. So that, the light emitted from the light emitting unit 3 for detection of filled amount is irradiated onto each liquid-filling container B to be transmitted therethrough to be then received by the light receiving unit 4 for detection of filled amount and based on the information about this received light, determination is made by the controller 11 whether the filled amount of the beverage W in each liquid-filling container B is within a predetermined range or not.

Also, the light emitted from the light emitting unit 6 for detection of liquid foreign substance is irradiated onto each liquid-filling container B to be transmitted therethrough to be then received by the light receiving unit 7 for detection of liquid foreign substance and based on the information about this received light, determination is made by the controller 11 whether any foreign substance is present in the liquid adjacent the bottom of each liquid-filling container B or not.

Further, the light emitted from the light emitting unit 9 for detection of container mouth is irradiated onto each liquid-fillng container B to be reflected therefrom to be then received by the light receiving unit 10 for detection of container mouth and based on the information about this received light, determination is made by the controller 11 whether the cap C is properly attached to the mouth of the liquid-filling container B or not.

The light emitting unit 3 for detection of filled amount comprises a light emitter 3A which includes a number of LED 3a arranged in a plate-like format. Similarly, the light emitting unit 6 for detection of liquid foreign substance comprises a light emitter 6A which includes a number of LED 6a arranged in a plate-like format. If necessary, on the front side of each of these light emitters 3A, 6A, there may be provided a diffuser plate 14 formed of an acrylic plate of a milky white color in order to assure uniform light irradiation.

Further, the light emitting unit 9 for detection of container mouth too comprises a light emitter 9A which includes a number of LED 9a arranged in a plate-like format. In this case too, if necessary, there may be provided a diffuser plate 16 formed of a milky white acrylic plate for assuring uniform light irradiation.

The light irradiated from the filled-amount detecting light emitter 3A is a near infrared light having a wavelength of 700 nm to 800 nm. The light irradiated from the liquid foreign substance detecting light emitter 6A is a near infrared light having a wavelength of 800 nm to 900 nm.

The light irradiated from the container-mouth detecting light emitter 9A is a visible light having a wavelength of 400 nm to 700 nm.

The filled-amount detecting light receiving unit 4 includes a light receiver 4A comprising e.g. a CCD camera and a light-receiving cut filter 17 disposed on the front side of the light receiver 4A. The cut filter 17 is provided as a filter adapted for selectively transmitting a predetermined wavelength alone, i.e. the near infrared light having a wavelength shorter the range of 700 nm to 800 nm.

Similarly, the liquid foreign substance detecting light receiving unit 7 includes a light receiver 7A comprising e.g. a CCD camera and a light-receiving cut filter 7B disposed on the front side of the light receiver 7A This cut filter 7B is provided as a filter adapted for selectively transmitting the near infrared light having a wavelength shorter than the range of 800 nm to 900 nm alone.

Further, the container mouth detecting light receiving unit 10 includes a light receiver 10A comprising e.g. a CCD camera and a light-receiving cut filter 19 disposed on the front side of the light receiver 10A. This cut filter 19 is provided as a cut filter adapted for selectively transmitting the visible light having a wavelength shorter than the range of 400 nm to 700 nm alone.

Figure 2:
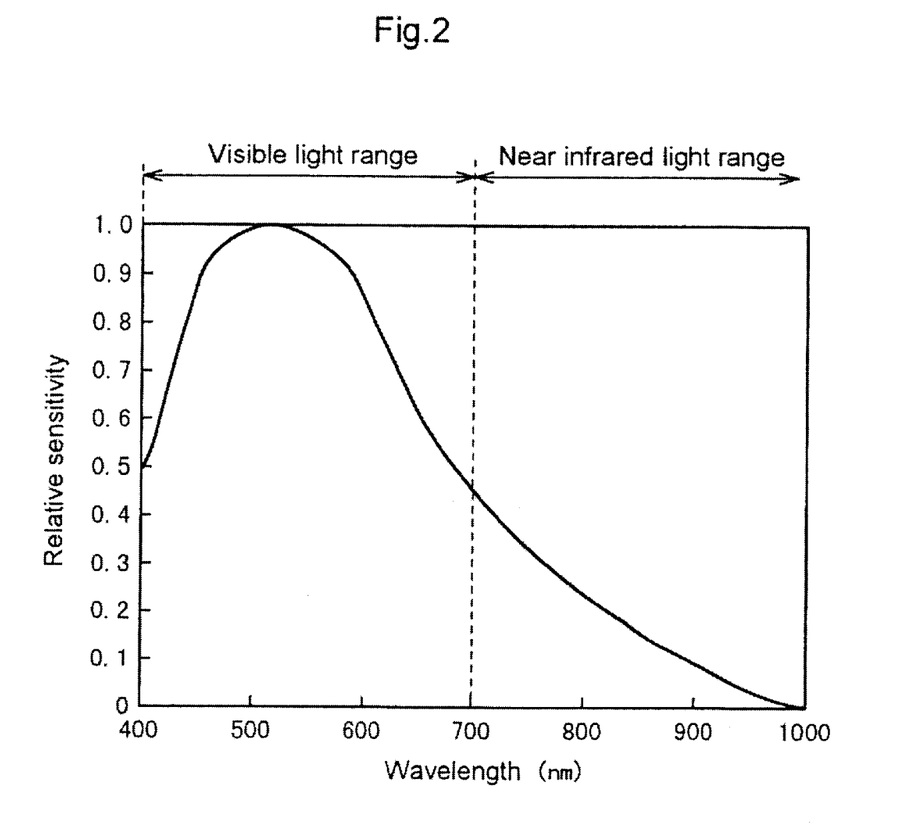
FIG. 2 is a graph showing characteristics of a CCD camera.

Incidentally, as shown in a graph in FIG. 2, such CCD camera exhibits a lower relative sensitivity for the near infrared radiation range than for the visible light range. However, any CCD cameras can be employed as long as their wavelength ranges between 700 nm and 900 nm.

According to this embodiment, onto each liquid-filing container B conveyed on the transfer conveyer 1, the filled-amount detecting light emitting unit 3 emits and irradiates the near infrared light having a wavelength of 700 nm to 800 nm alone, the liquid foreign substance detecting light emitting unit 6 emits and irradiates the further infrared light having a wavelength of 800 nm to 900 nm alone and the container mouth detecting light emitting unit 9 emits and irradiates the visible light having a wavelength of 400 nm to 700 nm alone, respectively and simultaneously.

The near infrared light from the filled-amount detecting light emitting unit 3 and the further near infrared light from the liquid foreign substance detecting light emitting unit 6 are transmitted through the liquid-fillng container B to be received by the filled-amount detecting light receiving unit 4 and the liquid foreign substance detecting light receiving unit 7, respectively. Further, the visible light from the container mouth detecting light emitting unit 9 is reflected by the cap C to be received by the container mouth detecting light receiving unit 10.

Then, the information of these lights received respectively by the three light receiving units 4, 7, 10 are sent to the controller 11, so that this controller 11 determines the filled amount of the beverage W in the liquid-filling container B based on the received light information from the filled-amount detecting light receiving unit 4, i.e. whether the liquid level of the beverage W is within a predetermined range or not and determines also presence/absence of any foreign substance in the liquid, i.e. beverage in the liquid-filling container B based on the received light information from the liquid foreign substance detecting light receiving unit 7 and the controller further determines whether the cap C is properly attached to the mount of the container B or not, based on the received light information from the container mouth detecting light receiving unit 10.

If any liquid-filling container B is detected to contain more than the predetermined range of beverage W or any foreign substance mixed in the beverage W or have improper attachment of the cap C, then, a certain appropriate measure will be taken, such as automatic removal of this liquid-filling container B away from the conveyer 1 or issuance of an alarm by means of an alarming device.

[Other Embodiments]

(1) In the foregoing embodiment, three detecting devices of the filled-amount detecting device 2, the liquid foreign substance detecting device 5 and the container mouth detecting device 8 are provided. Instead, the present invention may be embodied with providing two of them, i.e. the filled-amount detecting device 2 and the liquid foreign substance detecting device 5 alone or the filled-amount detecting device 2 and the container mouth detecting device 8 alone or the liquid foreign substance detecting device 5 and the container mouth detecting device 8 alone.

Further alternately, the invention may be embodied also with providing a further detecting device other than the filled-amount detecting device 2 and the liquid foreign substance detecting device 5. An example of such modified embodiment is illustrated in FIG. 3.

Next, this modified embodiment will be described with reference to FIG. 3. In the following description, in order to avoid redundancy of description, the same components and components having the same function as those employed are denoted with identical reference marks or numerals and description of them will be omitted. The following description concerns mainly those portions different from the foregoing embodiment only.

In this further embodiment, in place of the filled-amount detecting device 2 and the liquid foreign substance detecting device 5, there is provided a container/container-material foreign substance detecting device 20 as an imaging device for detecting whether any foreign substance was inadvertently mixed in the material forming each liquid-filling container B during the previous stage of manufacture. This container/container-material foreign substance detecting device 20 similarly includes a light emitting unit 21 and a light receiving unit 22 which are disposed in opposition to each other across the transfer conveyer 1.

The light emitting unit 21 comprises a light emitter 21A which includes a number of LED 21a arranged in a plate-like format. The irradiated light from this light emitter 21A is a near infrared light having a wavelength of 700 to 900 nm. The light receiving unit 22 includes a light receiver 22A comprising a CCD camera and a light-receiving cut filter 24 disposed on the front side of the light receiver 22A. This cut filter 24 is provided as a filter adapted for selecting transmitting the near infrared light having a wavelength of 700 to 900 nm alone.

Therefore, according to this further embodiment, for each liquid-filling container B conveyed by the transfer conveyer 1, the light emitting unit 21 for detection of foreign substance in the container material emits and irradiates the near infrared light having a wavelength of 700 to 900 nm and the container mouth detecting light emitting unit 9 emits and irradiates the visible light having a wavelength of 400 to 700 nm, respectively and simultaneously. And, the near infrared light from the container/container-material foreign substance detecting light emitting unit 21 is transmitted through the liquid-filling container B to be received by the light receiving unit 22 corresponding thereto, while the visible light from the container mouth detecting light emitting unit 9 is reflected by the cap C to be received by the light receiving unit 10 corresponding thereto.

Thereafter, like the foregoing embodiment, the controller 11 effects determination about presence/absence of foreign substance mixed in the material forming the liquid-filling container B, based on the received light information from the container/container-material foreign substance detecting light receiving unit 22 and also determination as to whether the cap C is properly attached or not, based on the received light information from the container mouth detecting light receiving unit 10, respectively. Then, based on the results of these determinations, some appropriate measure will be taken.

Incidentally, in this modified embodiment shown in FIG. 3, the container/container-material foreign substance detecting device 20 picks out the entire image of the liquid-filling container B. Therefore, based on the received light information from this container/container-material foreign substance detecting device 20, the controller 11 can be modified to detect not only presence/absence of foreign substance in the container B material, but also other conditions as well at the same time.

That is to say, by using the apparatus having the construction of FIG. 3 as it is, it is possible to adapt the single detecting device 20 to detect both the presence/absence of foreign substance in the material forming the liquid-filling container B and the presence/absence of foreign substance in the liquid or to detect both the presence/absence of foreign substance in the material forming the liquid-filling container B and the filled amount or both the presence/absence of foreign substance in the liquid and the filled amount.

Moreover, by using the apparatus having the construction of FIG. 3 as it is, it is also possible to detect the presence/absence of foreign substance in the material forming the liquid-filling container B and the presence/absence of foreign substance in the liquid-filling container B individually or simultaneously with detection of the condition of the mouth of the liquid-filling container B.

That is to say, in the embodiment of FIG. 3, various conditions are detected for each liquid-filling container B which was filled with the beverage W and fitted with the cap C. Instead, the construction may be used also in a system in which a plurality of empty liquid-filling containers having no beverage W filled therein and no caps C attached thereto are conveyed in succession by the transfer conveyer 1.

In adopting such construction, for instance, the near infrared light from the foreign substance detecting light emitting unit 21 is transmitted through the empty container B to be received by the foreign substance detecting light receiving unit 22 for detection of any foreign substance in the material forming the liquid-filling container B and further detection of foreign substance inside the container B. Thus, by using such foreign substance detecting device 20 shown in FIG. 3, the detection of presence/absence of foreign substance in the material of the liquid-filling container B and the further detection of presence/absence of foreign substance inside the liquid-filling container may be effected individually or simultaneously. For this reason, this foreign substance detecting device 20 is generically referred to as a "container/container-material foreign substance detecting device".

Further, the visible light from the container mouth detecting light emitting unit 9 is reflected by the mouth of the empty liquid-filling container B to be received by the container mouth detecting light receiving unit 10 for detection of presence/absence of a nick, flaw or stain at the mouth of the empty container B.

(2) In the foregoing embodiments, each of the light receivers 3A, 6A, 9A, 21A is constituted from a number of LED 3a, 6a, 9a, 21a arranged in a plate-like format. Instead, it is also possible to adapt the light emitter to emit only a light of a predetermined wavelength, by e.g. forming the unit of a near-infrared light emitting diode.

Moreover, the light emitting unit may include a light emitter element having a wide range of wavelength, such as a conventional incandescent electric lamp, a fluorescent lamp, a stroboscopic lamp, etc. Then, if a diffuser plate is provided on the front side of this light emitter, a light-emitter cut filter for selective transmission of a predetermined wavelength light component may be provided in front of or behind the diffuser plate.

(3) In case the filled-amount detecting light emitter 3A and the liquid foreign substance detecting light emitter 6A are provided like the above embodiment, these two light emitters 3A, 6A may be provided as a single integrated unit. That is, a single light emitter for emitting light having a wide range of wavelength is provided and a light-emitting cut filter for selective transmission of the near infrared light having a wavelength shorter than the range of 700 nm to 800 nm alone is provided upwardly of and on the front side of the emitter, so as to provide a filled-amount detecting light emitter 3A together. Further, downwardly thereof, another light-emitting cut filter 13 for selective transmission of the near infrared light having a wavelength of 800 nm to 900 nm alone is provided to constitute the liquid foreign substance detecting light emitter 6A.

(4) In the foregoing embodiments described above, a glass bottle is used as an example of the liquid-filling container B. The invention is not limited thereto. The invention may find utility also for other types of containers or bottles made of other material such as a synthetic resin, exemplified by a PET bottle. Also, in this invention, the type of liquid W is not particularly limited to the beverage. The invention is usefull for any other kind of liquid than beverages.

Further, the foregoing description concerns a construction for use in a manufacturing line for successively filling a plurality of liquid-filling containers B being conveyed one after another. Instead, the invention may find utility also in a construction in which the filled amount in the container B, the presence/absence of foreign substance in the liquid, inside the container or in the container material and the attachment condition of the cap are detected individually for each liquid-filling container B filled with the liquid W. Further, the invention may find utility also in a construction the presence/absence of foreign substance in the container or the container material, the condition of the container mouth etc. are detected individually for each empty liquid-filling container B.

(5) In the foregoing embodiments, the light emitting units 3, 6, 21 irradiate near infrared lights and the light receiving units 4, 7, 22 receive these near infrared lights. Instead, it is also possible to adapt the light emitting units 3, 6, 21 to respectively irradiate a light containing a greater amount of infrared light component than visible light component and/ or to adapt the light receiving units 4, 7, 22 to receive a light containing a greater amount of infrared light component than visible light component.

INDUSTRIAL APPLICABILITY OF THE INVENTION

As described above, the method and apparatus of the invention for imaging a liquid-filled container is suitable, in particular, for a manufacturing line of various beverages such as soft drinks or alcoholic beverages in order to inspect whether the amount of liquid as the beverage filled in the container is within a predetermined range or not and/or whether any foreign substance is inadvertently mixed in the beverage filled in the container or present in the container or the material forming the container or the condition of the mouth of the container or whether a cap is securely fitted on the mouth of the container or not.

What is claimed is:

1. A method of imaging a liquid-filling container with a plurality of imaging devices, each imaging device including a light emitting unit and a light receiving unit, comprising the steps of:
   a) irradiating light from each light emitting unit onto the liquid-filling container; and
   b) receiving at each light receiving unit the light transmitted through or reflected from the liquid-filling container,
   wherein said plurality of imaging devices differ from each other in optical axes and wavelengths of the lights irradiated by the respective light emitting units and received by the respective light receiving units corresponding thereto; and
   said plurality of imaging devices are used for different detection purposes associated with said liquid-filling container.

2. The method of claim 1, wherein said light emitting units respectively have light emitters each capable of emitting and irradiating light of a predetermined wavelength and the light receiving units respectively have light-receiving cut filters for allowing transmission of a light in the predetermined wavelength and light receivers for receiving the light transmitted through the respective light-receiving cut filters corresponding thereto.

3. The method of claim 1, wherein at least one of said light emitting units emits and irradiates near infrared light.

4. The method of claim 1, wherein at least one of said light receiving units receives near infrared light.

5. The method of claim 1, wherein each of the plurality of imaging devices images a state of liquid-filling containers which are conveyed one after another along a conveying line.

6. The method of claim 1, wherein one of said plurality of imaging devices is a filled-amount detecting device for detecting the filled amount of the liquid filled in the container.

7. The method of claim 1, wherein one of said plurality of imaging devices is a liquid foreign substance detecting device for detecting foreign substance present in the liquid filled in the container.

8. The method of claim 1, wherein one of said plurality of imaging devices is a container/container material foreign substance detecting device for detecting foreign substance present in the container or in material forming the container.

9. The method of claim 1, wherein one of said plurality of imaging devices is a container-mouth detecting device for detecting condition of a mouth of the container or attachment condition of a cap to the container mouth.

10. The method of claim 1, wherein each said light emitting unit comprises a light emitter including a number of LEDs arranged in a plate-like format.

11. An apparatus for imaging a liquid-filling container comprising a plurality of imaging devices, each imaging device including a light emitting unit and a light receiving unit, the apparatus irradiating light from each light emitting unit onto the liquid-filling container and receiving at each light receiving unit the light transmitted through or reflected from the liquid-filling container,
   wherein said plurality of imaging devices differ from each other in optical axes and wavelengths of the lights irradiated by the respective light emitting units and received by the respective light receiving units corresponding thereto; and
   said plurality of imaging devices are used for different detection purposes associated with said liquid-filling container.

12. The apparatus of claim 11, wherein said light emitting units respectively have light emitters each capable of emitting and irradiating light of a predetermined wavelength and the light receiving units respectively have light-receiving cut filters for allowing transmission of a light in the predetermined wavelength and light receivers for receiving the light transmitted through the respective light-receiving cut filters corresponding thereto.

13. The apparatus of claim 11, wherein at least one of said light emitting units emits and irradiates near infrared light.

14. The apparatus of claim 11, wherein at least one of said light receiving units receives near infrared light.

15. The apparatus of claim 11, wherein each of the plurality of imaging device images a state of each of liquid-filling containers which are conveyed one after another along a conveying line.

16. The apparatus of claim 11, wherein one of said plurality of imaging devices is a filled-amount detecting device for detecting the filled amount of the liquid filled in the container.

17. The apparatus of claim 11, wherein one of said plurality of imaging devices is a liquid foreign substance detecting device for detecting foreign substance present in the liquid filled in the container.

18. The apparatus of claim 11, wherein one of said plurality of imaging devices is a container/container material foreign substance detecting device for detecting foreign substance present in the container or in material forming the container.

19. The apparatus of to claim 11, wherein one of said plurality of imaging devices is a container-mouth detecting device for detecting condition of a mouth of the container or attachment condition of a cap to the container mouth.

20. The apparatus of claim 11, wherein each said light emitting unit comprises a light emitter including a number of LEDs arranged in a plate-like format.

* * * * *

UNITED STATES PATENT AND TRADEMARK OFFICE
CERTIFICATE OF CORRECTION

PATENT NO.   : 6,753,527 B1
DATED        : June 22, 2004
INVENTOR(S)  : Yamagishi et al.

It is certified that error appears in the above-identified patent and that said Letters Patent is hereby corrected as shown below:

<u>Title page,</u>
Item [22], PCT Filed: "Jan. 2, 2001" should read -- Feb. 1, 2001 --

<u>Column 12,</u>
Line 56, "apparatus of to claim 11" should read -- apparatus of claim 11 --

Signed and Sealed this

Thirtieth Day of November, 2004

JON W. DUDAS
*Director of the United States Patent and Trademark Office*